United States Patent [19]
Graf et al.

[11] Patent Number: 5,544,520
[45] Date of Patent: Aug. 13, 1996

[54] BRIDGE PERMEAMETER

[75] Inventors: Darin C. Graf, Edgewood; Norman R. Warpinski, Albuquerque, both of N.M.

[73] Assignee: Sandia Corporation, Albuquerque, N.M.

[21] Appl. No.: 386,836

[22] Filed: Feb. 10, 1995

[51] Int. Cl.$^6$ ................................................. G01N 15/08
[52] U.S. Cl. .............................................................. 73/38
[58] Field of Search ............................. 73/38, 37, DIG. 8

[56] References Cited

U.S. PATENT DOCUMENTS

| | | | |
|---|---|---|---|
| 2,618,151 | 11/1952 | Leas | 73/38 |
| 2,842,958 | 7/1958 | Sayre, Jr. et al. | 73/38 |
| 3,162,037 | 12/1964 | Hurst | 73/38 |
| 4,555,934 | 12/1985 | Freeman et al. | 73/38 |
| 4,573,342 | 3/1986 | Jones | 73/38 |
| 5,297,420 | 3/1994 | Gilliland et al. | 73/38 |

FOREIGN PATENT DOCUMENTS

| | | | |
|---|---|---|---|
| 229002 | 2/1969 | U.S.S.R. | 73/38 |
| 1004206 | 9/1965 | United Kingdom | 73/38 |

OTHER PUBLICATIONS

Graf, D. C. and Warpinski, N. R., "The Bridge Permeameter; An Alternative Method for Single-Phase, Steady-State Permeability Measurements," Sandia Report Sand93-4023, Sandia National Laboratories. (Distributed by printer on or after Feb 14, 1994.).

Recommended Practice for Determining Permeability of Porous Media, American Petroleum Institute, 1956.

Holman, J. P., "Experimental Methods for Engineers," McGraw-Hill, 1989, pp. 114–117 and 404, 405.

Gurley Testing Instruments, "The Gurley Permeometer", Bulletin No. 1400, published on or before 01 Dec. 1957, pp. 16–17.

*Primary Examiner*—Hezron E. Williams
*Assistant Examiner*—Daniel S. Larkin
*Attorney, Agent, or Firm*—George H. Libman

[57] ABSTRACT

A system for single-phase, steady-state permeability measurements of porous rock utilizes a fluid bridge arrangement analogous to a Wheatstone bridge. The arms of the bridge contain the sample and calibrated flow resistors.

8 Claims, 3 Drawing Sheets

BRIDGE PERMEAMETER

The United States Government has rights in this invention pursuant to Department of Energy Contracts No. DE-AC04-76DP00789 and DE-AC04-94AL85000 with the American Telephone and Telegraph Company and Sandia Corporation, respectively.

BACKGROUND OF THE INVENTION

The permeability of porous rock is an indication of the rate at which fluid will flow through the rock. Laboratory measurements of single-phase, steady-state permeability of porous rock are important for a number of different applications. The oil and gas industry uses permeability data as a key indicator of the ability of a hydrocarbon reservoir to be productive. In addition, the effective containment of large volumes of oil in underground salt caverns is directly dependent upon the permeability of the adjacent cavern walls. In addition, safe, long term underground isolation of radioactive and hazardous waste is contingent upon the flow and transport characteristics of the surrounding geologic formations.

There are two types of permeability tests that are typically performed today: the steady-state test and the pulse test. The steady-state test consists of measuring the flow rate and pressure drop across a rock sample under conditions of steady pressure. Steady-state techniques can be used for all rocks under all conditions, but this test is difficult and time consuming, especially for low permeability rocks, because steady conditions must be achieved and the flow rate must be measured. The pulse test is performed by subjecting a rock to an average pore pressure, opening a reservoir of known volume at a higher (or lower) pressure, and measuring the change in pressure as fluid flows into (or out of) the rock sample. This test requires no flow measurement and works well for higher permeability rocks where the permeability is it, sensitive to pressure and small pressure changes (between the reservoir and the initial pore pressure) can be used. However, for rocks that exhibit significant stress sensitivity (low-permeability and naturally fractured samples), the pulse technique may be less accurate because the permeability within the sample may be changing, and this is not accounted for by the analysis. For this and other reasons, there are many applications where steady-state measurements are preferred to pulse measurements.

The equipment for single-phase, steady-state measurements typically includes a bank of mass flow meters, a differential pressure transducer, and a back pressure regulator valve. This arrangement uses an inert gas such as nitrogen for the fluid media pumped through the sample because the inert gas will not react with constituents of the rock sample and change the rock's flow properties. Difficulties arise with this arrangement because high differential pressures and low flow rates are required when testing lower permeability rocks. Flow rates tend to approach the lower limit of the commercially available flow meters, requiring that the driving pressure, or $\Delta p$, be raised even higher so that a measurable level of flow can be maintained through the sample. However, as the pressure gradient across the sample increases, the stress gradient within the sample increases, resulting in significant deviations from in situ conditions.

A second problem with this method concerns the associated costs involved with purchasing and maintaining the mass flow meters. To cover the permeability ranges of interest, a typical permeameter incorporates three to five flow meters, with each flow meter costing up to $2000. Also, such flow meters require frequent and expensive calibration to maintain reliable accuracy, adding a periodic cost to conducting the measurements. Finally, these frequent calibrations can lead to significant down time for the permeameter system, further impeding cost effective and timely results.

Other examples of prior art methods of measuring permeability of porous rock are described in U.S. Pat. No. 4,555,934 of Garland et al. and U.S. Pat. No. 4,573,342 of Jones.

SUMMARY OF THE INVENTION

It is an object of this invention to provide an alternative process for single-phase, steady-state permeability measurements.

It is another object of this invention to provide lower cost apparatus for single-phase, steady-state permeability measurements.

Additional objects, advantages, and novel features of the invention will become apparent to those skilled in the art upon examination of the following description or may be learned by practice of the invention. The objects and advantages of the invention may be realized and attained by means of the instrumentalities and combinations particularly pointed out in the appended claims.

To achieve the foregoing and other objects, and in accordance with the purpose of the present invention, as embodied and broadly described herein, the present invention may comprise a fluid bridge for measuring the permeability of a material and having a plurality of paths for a test fluid, one of the paths holding a sample of the material so that fluid in the path passes through the sample. The other paths include flow resistors having a predetermined resistance to fluid flow. The permeability of the sample is determined from measured pressure drops, predetermined resistances, and fluid viscosity at the resistances.

BRIEF DESCRIPTION OF THE DRAWINGS

The accompanying drawings, which are incorporated in and form part of the specification, illustrate an embodiment of the present invention and, together with the description, serve to explain the principles of the invention.

DETAILED DESCRIPTION OF THE INVENTION

In accordance with this invention, the single-phase, steady-state permeability of tight rock can be measured without the use of expensive and troublesome mass flow meters. As disclosed herein, a bridge configuration of flow resistors and a standard hydrostatic pressure cell provides sufficient information from differential pressure measurements across the bridge network for the determination of the permeability of the tight rock sample in the pressure cell.

The measurement method is analogous to the Wheatstone Bridge commonly used to measure electrical resistivity changes in resistance-type strain gauges.

Figure 1:
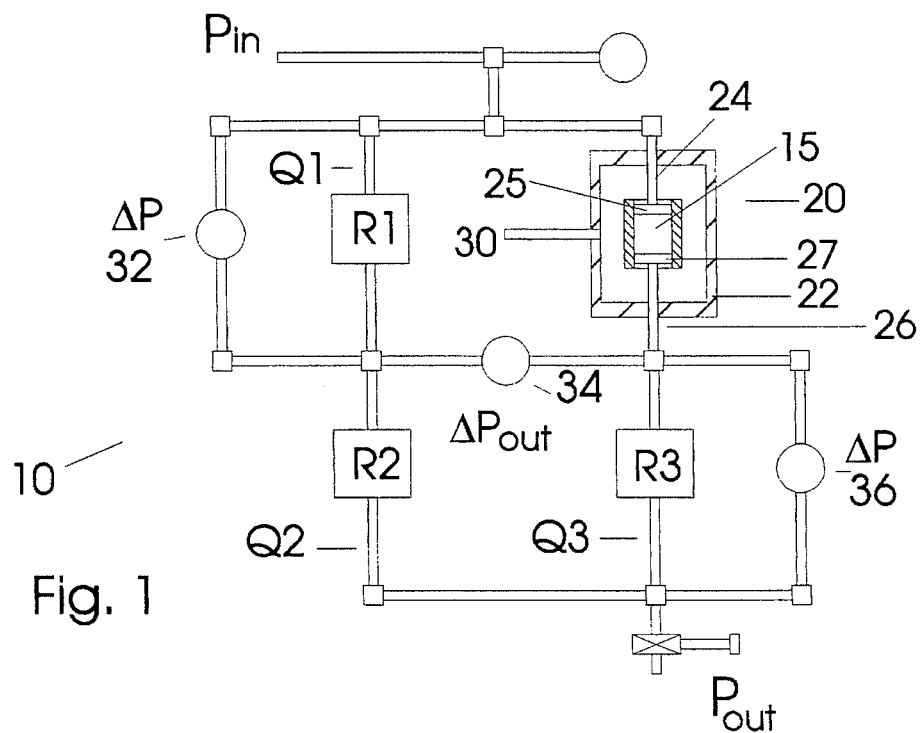
FIG. 1 shows a schematic representation of a bridge permeameter in accordance with this invention.

As shown in FIG. 1, fluid bridge circuit 10 includes flow resistors $R_1$, $R_2$, and $R_3$, each resistor having a fluid input and a fluid output, and a hydrostatic pressure cell 20 having a having a fluid input and a fluid output. (A flow resistor is described in more detail below.) The inputs of resistor $R_1$ and cell 20 are connected through fluid conveying means such as pipes to a source of fluid pressure, $P_{in}$. A differential fluid pressure gauge 32 is connected across resistor $R_1$, and a second differential pressure gauge 34 is connected between the outputs of resistor $R_1$ and cell 20. The input of resistor $R_2$ is connected in series with the output of resistor $R_1$, and resistor $R_3$ is connected in series with the output of cell 20. The outputs of resistors $R_2$ and $R_3$ connect together to the output $P_{out}$ of bridge 10. A third differential pressure gauge 36 is connected across resistor $R_3$.

A typical differential pressure gauge includes a housing having two inlets and a fluid path between the inlets blocked by a diaphragm. Movement of the diaphragm is indicated by the output of a strain gauge on the diaphragm. The construction of a differential pressure gauge is well known in the art and is not part of this invention.

Hydrostatic pressure cell 20 may be of conventional design and includes a pressure chamber 22. A cylindrical core of rock sample 15, surrounded by a sleeve 28 made of fluid-impermeable material such as rubber, is placed inside chamber 22. Input pipe 24 directs fluid from source $P_{in}$ to one end of sample 15 through a manifold 25. Fluid passing through sample 15 to its other end passes through manifold 27 to outlet pipe 26. Pressure is applied to housing 22 through inlet 30 to simulate the pressure on the sample at its normal depth in the ground.

For the circuit of FIG. 1, a derivation for a relationship between the permeability of sample 15, $k_s$, and differential bridge pressure measured at gauge 34, $\Delta P_{out}$, is analogous to the derivation for an electrical bridge network. The concept incorporates summation of pressure rises and drops around the bridge, then solving for the unknown permeability of sample 15 in hydrostatic pressure cell 20.

As shown by the American Petroleum Institute, *Recommended Practice for Determining Permeability of Porous Media*, 1956, pp. 5–7, Darcy's Law for single-phase, steady-state, viscous flow through porous media is $$\Delta p = \frac{Q \mu L}{k_s A} \qquad (1)$$

where $k_s$=sample permeability; $\mu$=fluid viscosity; $Q$=flow rate; $L$=sample length; $A$=sample cross section; and $\Delta p$=pressure drop across the sample. A characteristic resistance, $R_g$, can be defined as $$R_g = \frac{L}{kA} \qquad (2)$$

By substituting equation 2 into equation 1, the pressure drop across the sample may be defined as a function of characteristic resistance $$\Delta p = Q \mu R_g \qquad (3)$$

Adding pressure rises and drops around the bridge yields $$\Delta P_{out} = \Delta p_3 - \Delta p_2 \qquad (4)$$

where $\Delta p_3$ and $\Delta p_2$ are the pressure drops across $R_3$ and $R_2$, respectively, and $\Delta p_{out}$ is the pressure drop across gauge 34. Substituting equation 3 into equation 4 yields $$\Delta p_{out} = Q_3 \mu_3 R_3 - Q_2 \mu_2 R_2 \qquad (5)$$

Because mass is conserved on each side of the bridge, $Q_1 = Q_2$ and $Q_g = Q_3$. Therefore, flow rate through each side of the bridge is $$Q = \frac{\Delta p_{in}}{\mu_{av} R_{sum}} \qquad (6)$$

where $R_{sum}$ is the sum of the two resistors on one side of the bridge, added in series. The average viscosity, $\mu_{av}$, for the fluid flowing through each side of the bridge is taken as $(\mu_x + \mu_y)/2$, where the subscripts x and y correspond to 1 and 2 for the left side of the bridge, and 3 and g for the right side of the bridge. This calculation assumes a linear relationship between viscosity and pressure, which introduces an insignificant error for changes of gas pressure of less than a few hundred psi.

By substituting the general form of equation 6 for $Q_3$ and $Q_2$ into equation 5 and factoring out common terms, a relationship between differential bridge pressure and sample resistance, $R_g$, is obtained such that $$\Delta p_{out} = \frac{\Delta p_{in}}{\mu_{\Delta pav}} \left[ \frac{\mu_3 R_3}{R_3 + R_g} - \frac{\mu_2 R_2}{R_1 + R_2} \right] \qquad (7)$$

where $\Delta p_{out}$ is the pressure drop across the inner nodes of the bridge; $\Delta p_{in}$ is the pressure drop across the entire bridge; $R_g$ is the resistance of sample 15; $\mu_{\Delta pav}$ is the viscosity at the average bridge pressure; $\mu_2$ is the viscosity at the average pressure at $R_2$; and $\mu_3$ is the viscosity at the average pressure at $R_3$.

Since sample resistance $R_g$ was defined in equation 2, equation 7 is solved for $R_g$ $$k_s = \frac{L}{A} \left[ \left\{ \left( \frac{\Delta p_{out} \mu_{\Delta pav}}{\Delta p_{in}} + \frac{\mu_2 R_2}{R_1 + R_2} \right)^{-1} \mu_3 R_3 \right\} - R_3 \right]^{-1} \qquad (8)$$

Equation 8 provides a direct relationship between sample permeability and differential bridge pressures given that $R_1$, $R_2$, and $R_3$ are known and $\mu_{\Delta pav}$, $\mu_2$, $\mu_3$ can be calculated by knowing the average pressures at the indicated bridge points.

For compressible flow using inert gases, equation 8 is modified with a pressure ratio term as given in equation 9. This ratio is generally small, but can become large if the resistors are not sized properly for the application.

$$k_s = \frac{L}{A} \left[ \left\{ \left( \frac{\Delta p_{out} \mu_{\Delta pav}}{\Delta p_{in}} \cdot \frac{P_{out,av}}{P_{in}} + \frac{\mu_2 R_2}{R_1 + R_2} \right)^{-1} \mu_3 R_3 \right\} - R_3 \right]^{-1} \qquad (9)$$

where $P_{out, av}$ and $P_{in, av}$ are the average pore pressures at the $\Delta P_{out}$ and $\Delta P_{in}$ segments, respectively.

As shown by the derivation presented above, a key component to the invention is the flow resistor unit. These resistors could be other rock samples of known permeability, precision metering valves with known flow/pressure characteristics, or a small diameter orifice that can be characterized accurately for flow resistance. Of primary importance to any design is that the flow characteristics be highly repeatable and that the unit is not prohibitively costly. Another important consideration is that the unit be simple to set up, and that lengthy, repeated calibration procedures are avoided.

Figure 2A:
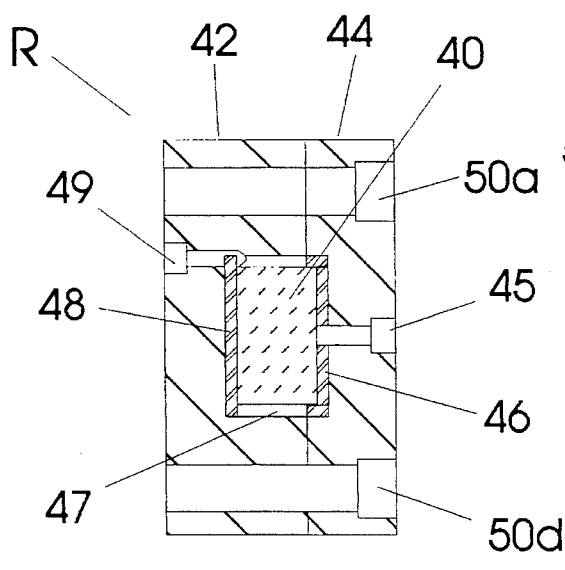
FIGS. 2A and 2B show a flow resistor for the bridge of FIG. 1.
Figure 2B:
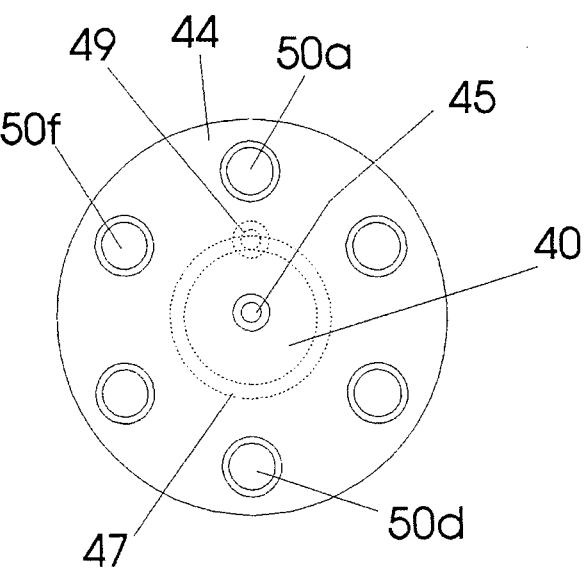

Because it is desirable for the resistors to have characteristics on the same order of magnitude of the sample under test, and because the rock samples of interest (such as sandstone) have permeability in the microDarcy range, core plugs formed of mineral materials having similar porosity properties are used to resist the passage of fluid in the resistors. A plug is held in the resistor structure shown in FIGS. 2A and 2B.

The disclosed resistor provides a core plug 40 shaped in the form of a cylinder with parallel ends that is placed in a holder having a first body portion 42 containing a cavity for plug 40 and a second body portion 44 covering the cavity and fastened to portion 42 by fasteners 50a–50f. Each end of plug 40 is covered by a fluid-impervious material 46, 48 such as rubber to direct the flow of fluid through plug 40. Fluid enters the resistor through an orifice 45; a hole is provided in material 46 to permit fluid to pass into the center of plug 40. Because materials 46 and 48 seal the ends of plug 40, fluid can only exit plug 40 along its diameter into space 47 between the edges of plug 40 and the cavity in body 42. An orifice 49 provides an exit for the fluid.

The intent of this particular design is to provide a simple and inexpensive means of flow resistance, one that can easily be reconfigured by merely changing the core plug.

A 1.00 inch diameter by 0.5 inch long chalk sample was selected for the initial set of characterization tests, because of chalk's relative insensitivity of permeability to stress variations. This characteristic is important because the resistance, L/(k.A), must be relatively constant over a range of pore pressures so that resistors can more easily be matched with the expected permeabilities of the unknown sample.

Figure 3A:
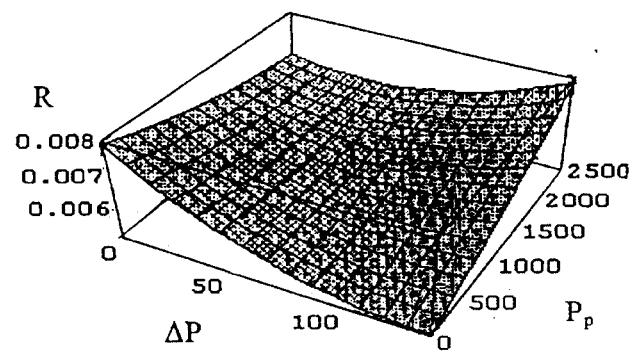
FIGS. 3A, 3B, and 3C show the operating characteristics of three resistors built in accordance with this invention.
Figure 3B:
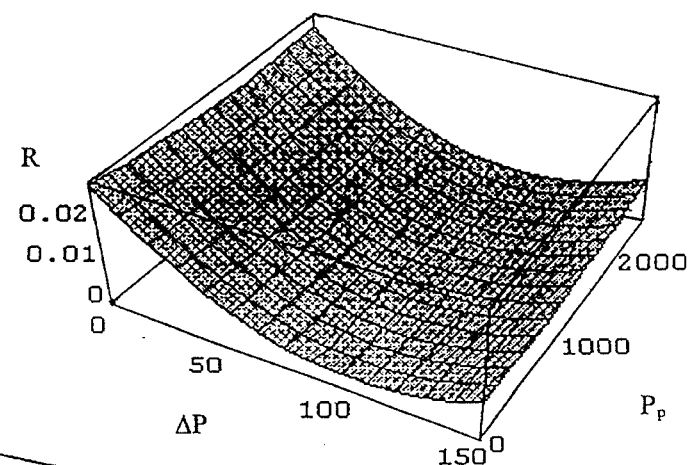
Figure 3C:
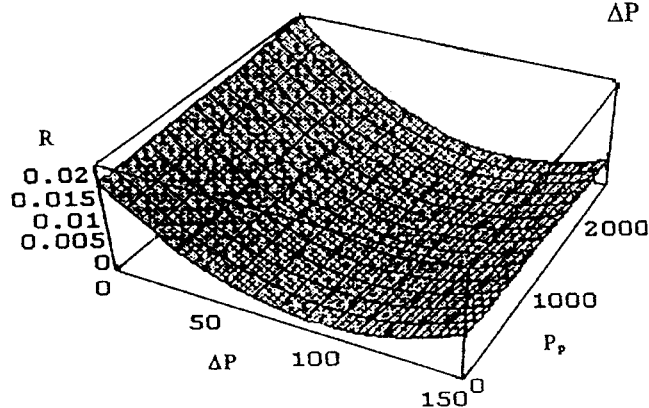

A series of flow tests have been conducted on three different resistors of this design, each resistor having a core plug made of chalk. The purpose of the tests was to characterize resistance, or R values, over a range of pore pressures and differential pressures. The results of these tests is illustrated in FIGS. 3A, 3B, and 3C for resistors $R_1$, $R_2$, and $R_3$, respectively. The data from these tests is provided in Appendix A, and shows that flow resistance can differ among samples constructed from the same batch of chalk.

Once a matrix of data for each resistor was obtained, a 3-dimensional curve-fit model (a standard mathematical procedure) was applied to yield a relationship of $$k = a_1 + a_2 \cdot \Delta p + a_3 \cdot P_p + a_4 \cdot \Delta p^2 + a_5 \cdot \Delta p \cdot P_p + a_6 \cdot P_p^2 \quad (10)$$

where k is the permeability at the given pressures; $\Delta p$ is the pressure drop across the resistor; $P_p$ is the average resistor pore pressure; and $a_1$, $a_2$, $a_3$, $a_4$, $a_5$, and $a_6$ are known coefficients. The coefficients of equation 10 are determined from the measured data.

Equation 10 can be solved for k, and substituted into equation 2 to provide resistance values for equation 9.

The values of the three resistors of FIGS. 3A–3C were as follows:

$R_1 = 0.008051 - (3.9811 \cdot 10^{-4})\Delta P + (1.4739 \cdot 10^{-7})\Delta P^2 - (8.109 \cdot 10^{-7})P_p + (1.0910 \cdot 10^{-8})\Delta P \cdot P_p + (1.2801 \cdot 10^{-10})P_p^2$.

$R_2 = 0.02797 - (5.0754 \cdot 10^{-4})\Delta P + (2.4662 \cdot 10^{-6})P^2 - (3.7423 \cdot 10^{-6})P_p + (7.8392 \cdot 10^{-9})\Delta P \cdot P_p + (1.0824 \cdot 10^{-9})P_p^2$.

$R_3 = 0.019698 - (3.9471 \cdot 10^{-4})\Delta P + (2.1746 \cdot 10^{-6})\Delta P^2 - (1.1539 \cdot 10^{-6})P_p + (1.8786 \cdot 10^{-8})\Delta P \cdot P_p + (4.9429 \cdot 10^{-11})P_p^2$.

Figure 4A:
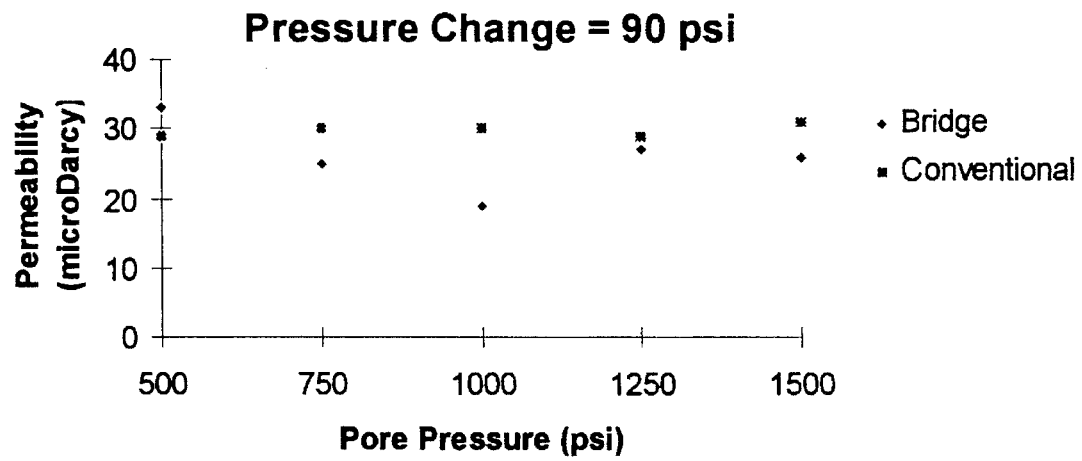
FIGS. 4A and 4B show permeability measurements made with the bridge of the invention and measurements made with prior art techniques at two differential pressures.
Figure 4B:
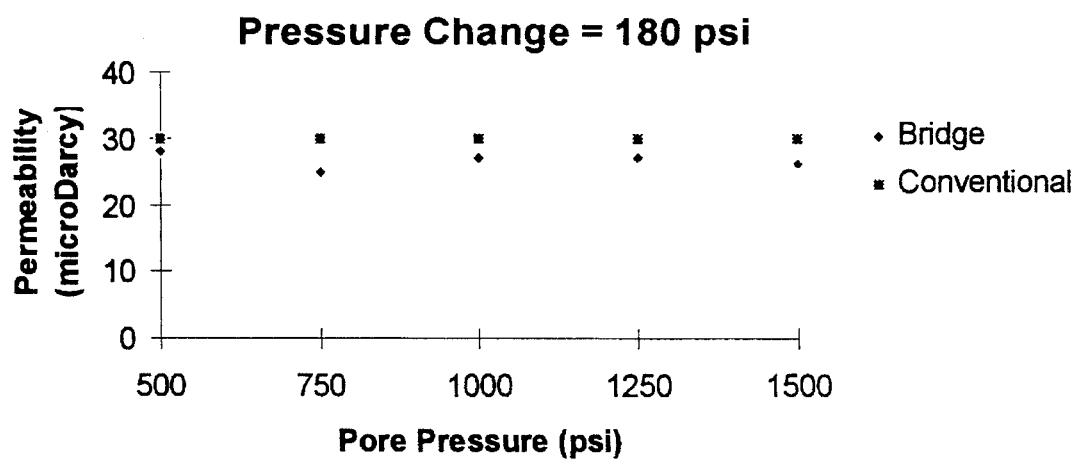

Using these resistance values, a series of laboratory tests were conducted to compare single-phase, steady-state permeability results from the bridge configuration to results obtained using conventional methods. FIGS. 4A and 4B show plots of permeability vs. pore pressure, at pressure drops across the sample of 90 psi and 180 psi, respectively. The data show reasonably consistent agreement between the two methods, with the bridge permeameter results generally falling within 10–15% of conventional results. However, a number of problems emerged while conducting the laboratory tests. The mass flow meters used in conjunction with the tests displayed some inconsistencies. For example, while switching between one flow meter with a range of 0–50 standard cubic centimeters per minute (SCCM) to another flow meter with a range 0–500 SCCM, an inconsistency of 5–10 SCCM between the readings of the two instruments was experienced. Because of this inconsistency in the instrumentation, small errors are likely to exist in the curve-fit models for the resistors, and thus also in the permeability results obtained using those models. This equipment problem could easily account for a significant portion of the discrepancy between results from the two methods.

Another possible reason for the disparity between the two measurements is the presence of turbulent flow at the entrance to the resistor. A hollow disk configuration would enlarge the entrance area and minimize turbulence effects, but whole disks were used in these experiments to minimize machining and subsequent damage to the resistor rock specimens.

The comparison between the two techniques shows agreement that is quite good for permeability measurements (for low permeability rocks, a factor of two difference between different techniques is commonly observed). Furthermore, if this technique is to be used commercially, it is likely that new resistors with more constant properties could be developed. Some examples of possible materials include ceramics, cements, resin coated sand, fused silica and sintered metals.

For practical application of this invention it will be necessary to document the sensitivity of permeability to resistance. While the sensitivities can be easily obtained from derivatives of equations 8 and 9, these sensitivities also require $\Delta p$, viscosity, and average pressure terms as well as the resistance terms. Different sets of resistors will probably be required to cover a full range of permeabilities normally encountered. As is the case with the known electrical Wheatstone bridge, accuracy will be enhanced if the values of $R_1$–$R_3$ are selected to minimize differential bridge pressure between the midpoints of the two bridge arms, as would be indicated by a null value at gauge 34.

The particular sizes and equipment discussed above are cited merely to illustrate a particular embodiment of this invention. It is contemplated that the use of the invention may involve components having different sizes and shapes as long as the principle of utilizing flow resistors in a bridge circuit is followed. It is intended that the scope of the invention be defined by the claims appended hereto.

APPENDIX A

| perm. (μDarcy) | pore press. (psi) | resistance (μDarcy$^{-1}$ cm$^{-1}$) | diff. press. (psi) |
| --- | --- | --- | --- |
| Resistor $R_1$ | | | |
| 36.4 | 2015.4 | 0.00688 | 9.5 |
| 37.7 | 2011.9 | 0.00664 | 81.2 |
| 38.2 | 2015.7 | 0.00656 | 96.8 |
| 39.3 | 2013.3 | 0.00637 | 33.7 |
| 37.6 | 1756.3 | 0.00666 | 10.7 |
| 39.9 | 1765.7 | 0.00644 | 59.4 |
| 39.6 | 1758.1 | 0.00632 | 100 |
| 36.6 | 1508.5 | 0.00684 | 13.6 |
| 40 | 1519.1 | 0.00626 | 60 |
| 40.1 | 1514.2 | 0.00624 | 104.6 |
| 37.1 | 1257.6 | 0.00675 | 12.6 |
| 41.1 | 1255 | 0.00609 | 62.2 |

APPENDIX A-continued

| perm. (μDarcy) | pore press. (psi) | resistance (μDarcy$^{-1}$ cm$^{-1}$) | diff. press. (psi) |
|---|---|---|---|
| 40.9 | 1254.5 | 0.00612 | 113.6 |
| 34.3 | 1002.4 | 0.00730 | 14.1 |
| 40.9 | 1010 | 0.00612 | 70.2 |
| 41 | 1011 | 0.00611 | 129.1 |
| 35.2 | 749.7 | 0.00711 | 14.9 |
| 41.5 | 755 | 0.00603 | 70.9 |
| 42.1 | 763.3 | 0.00595 | 132.9 |
| 35.9 | 500.1 | 0.00698 | 18.2 |
| 43.1 | 501.8 | 0.00581 | 79.2 |
| 43.5 | 503.7 | 0.00576 | 134.4 |

Resistor R$_2$

| | | | |
|---|---|---|---|
| 50.8 | 2508.9 | 0.00493 | 10.4 |
| 49.5 | 2517.5 | 0.00506 | 33.8 |
| 48.7 | 2514.7 | 0.00514 | 58.6 |
| 45.5 | 2519.3 | 0.00550 | 101 |
| 50.6 | 2262.1 | 0.00495 | 11.2 |
| 50.4 | 2260.5 | 0.00497 | 33.7 |
| 49.4 | 2263.5 | 0.00507 | 66.8 |
| 47.3 | 2262.7 | 0.00529 | 107.9 |
| 49 | 2012.4 | 0.00511 | 11.7 |
| 51 | 2009 | 0.00491 | 38.1 |
| 49.1 | 2012.9 | 0.00510 | 75.7 |
| 46.5 | 2016.4 | 0.00538 | 123.3 |
| 49.8 | 1759.9 | 0.00503 | 11.7 |
| 50 | 1764.1 | 0.00501 | 38.2 |
| 48.8 | 1761 | 0.00513 | 85.1 |
| 46.4 | 1759.5 | 0.00539 | 134.4 |
| 48.5 | 1507.4 | 0.00516 | 13.3 |
| 49.9 | 1500 | 0.00502 | 43 |
| 48.3 | 1514.2 | 0.00518 | 98.9 |
| 45 | 1512.1 | 0.00556 | 145.1 |
| 49.9 | 1258.2 | 0.00502 | 13.2 |
| 49.5 | 1257.9 | 0.00506 | 44.9 |
| 48.9 | 1267.9 | 0.00512 | 80 |
| 48.5 | 1255 | 0.00516 | 117.2 |
| 51.2 | 1004.3 | 0.00489 | 13.4 |
| 50.2 | 1004.6 | 0.00499 | 45.2 |
| 49.1 | 1007.1 | 0.00510 | 93 |
| 48.9 | 1002.6 | 0.00512 | 135.7 |
| 51.1 | 753.5 | 0.00490 | 10.9 |
| 50.2 | 761.6 | 0.00499 | 46.3 |
| 50.3 | 748.2 | 0.00498 | 97.3 |
| 46.7 | 748.2 | 0.00536 | 139.9 |
| 52.8 | 502.2 | 0.00474 | 12.1 |
| 50 | 510 | 0.00501 | 53.7 |

Resistor R$_3$

| | | | |
|---|---|---|---|
| 53.7 | 2516.8 | 0.00466 | 12.4 |
| 52.5 | 2521 | 0.00477 | 28.7 |
| 49.2 | 2513.4 | 0.00509 | 62.9 |
| 59.8 | 2506.8 | 0.00418 | 125.2 |
| 54.4 | 2023.8 | 0.00460 | 13 |
| 53.8 | 2010.8 | 0.00465 | 31.9 |
| 49.7 | 2012.9 | 0.00504 | 73.8 |
| 53.9 | 2004.4 | 0.00464 | 125.9 |
| 54.7 | 1504.6 | 0.00457 | 17.2 |
| 52.9 | 1517.6 | 0.00473 | 41.6 |
| 51.8 | 1508.2 | 0.00483 | 79.6 |
| 56.4 | 1505.4 | 0.00444 | 113.1 |
| 52.1 | 1007.8 | 0.00480 | 14.4 |
| 56.2 | 1008.9 | 0.00445 | 36 |
| 54.1 | 1003.1 | 0.00463 | 77.4 |
| 51.1 | 1010 | 0.00490 | 130.8 |
| 53.6 | 498.9 | 0.00467 | 20.9 |
| 63.6 | 503.9 | 0.00393 | 49.4 |
| 63.9 | 503.9 | 0.00392 | 74.6 |
| 64.1 | 495.7 | 0.00390 | 105 |

We claim:

1. Apparatus for measuring the permeability of a material comprising:

a fluid bridge having a plurality of paths for a test fluid, one of said paths including means for holding the material, whereby fluid in said one path passes through the material; and others of said paths including flow resistors having a predetermined resistance to fluid flow, whereby fluid in each of said other paths passes through a flow resistor; and means for determining the pressure drop across a plurality of said paths, the permeability of said material being a function of measured pressure drops, predetermined resistances, and fluid viscosity at said resistances.

2. The apparatus of claim 1 wherein each flow resistor comprises:

a housing made of a housing material impervious to the flow of the fluid, said housing having an interior cavity;

a plug of permeable resistance material in the cavity; and means for conducting fluid from an input port at a surface of said housing, through said permeable resistance material, and to an output port at a surface of said housing.

3. The apparatus of claim 2 wherein said housing may be opened to provide access to the cavity and closed to seal the cavity.

4. The apparatus of claim 2 wherein said cavity and said sample are cylindrical, the ends of said sample being sealed against the ends of the cavity, and said means for conducting fluid from an input port communicates with the cavity only at the end of the cavity adjacent said sample.

5. The apparatus of claim 4 wherein the diameter of the cavity is larger than the diameter of said sample thereby defining a volume between the outer surface of said sample and the cavity, and said means for conducting fluid from the output port communicates with the cavity only at the volume.

6. A method of determining the single phase, steady state permeability of a porous rock sample comprising:

forming a fluid bridge having a fluid input and a fluid output connected by two parallel fluid paths, each path having first and second fluid flow resistances connected in series at a path midpoint, wherein the sample is one of said resistances in one of said paths, the other resistances having known resistance values;

applying a fluid to the fluid input;

determining the sample resistance from the known resistances and measured fluid properties.

7. The method of claim 6 wherein said measured fluid properties include input and output fluid pressures and fluid viscosity within the bridge.

8. The method of claim 7 further comprising the step of adjusting the known resistance values to minimize the pressure difference between the midpoints of the two bridge arms.

* * * * *